United States Patent [19] [11] 4,143,087
Bamforth et al. [45] Mar. 6, 1979

[54] DIMERIZATION PROCESS

[75] Inventors: John R. Bamforth; Raymond Higgins, both of Middlesbrough, England

[73] Assignee: Imperial Chemical Industries Limited, London, England

[21] Appl. No.: 915,122

[22] Filed: Jun. 13, 1978

[30] Foreign Application Priority Data

Jun. 17, 1977 [GB] United Kingdom ............... 25441/77

[51] Int. Cl.$^2$ ............................................. C07C 3/20
[52] U.S. Cl. ............................................ 260/683.15 R
[58] Field of Search ............................... 260/683.15 R

[56] References Cited

U.S. PATENT DOCUMENTS 2,939,884  6/1960  Garrison ................... 260/683.15 R Primary Examiner—C. Davis
Attorney, Agent, or Firm—Cushman, Darby & Cushman

[57] ABSTRACT

Compounds of formula $R_1 R_2 C = CR_3 CHR_4 R_5$ wherein $R_1$, $R_2$, $R_3$, $R_4$ and $R_5$ are selected individually from hydrogen, akyl, aryl, cyano, cyclohexyl, halide groups and substituted derivatives of these groups are oxidatively dimerized in the presence of a partially reduced bismuth oxide catalyst, the average degree of reduction of bismuth oxide being 1 to 70%, and in the presence of oxygen, the oxygen conversion being in the range 90 to 99%.

11 Claims, No Drawings

DIMERIZATION PROCESS

THIS INVENTION relates to the oxidative dimerisation of olefinic compounds.

Several proposals have been made in the past for the oxidative dimerisation of olefin hydrocarbons, especially of the lower olefins. Regrettably, several of the methods proposed have not been very satisfactory and conversion to the dimeric compounds has only been accomplished at the expesnse of high costs and in low yield. For example, propylene has been converted in the vapour phase and in the presence of hydrogen peroxide to 1,5-hexadiene but yields are poor. More recently, rather more success has been achieved using certain oxide catalysts. For example, the olefin is contacted with oxygen and a catalytic amount of one or more metal oxides, for example oxides of bismuth, zinc, chromium, tungsten and so on.

According to the present invention a process for the oxidative dimerisation of a compound of general formula $R_1 R_2 C = CR_3 - CH.R_4R_5$ where $R_1$, $R_2$, $R_3$, $R_4$ and $R_5$ are selected individually from hydrogen, alkyl, aryl, cyano, cyclohexyl, halide groups and substituted derivatives of these groups comprises heating the compound $R_1 R_2 C = CR_3 - CH - R_4 R_5$ in the presence of a catalyst comprising bismuth oxide in partially reduced form, the average degree of reduction of bismuth oxide throughout the catalyst bed being at least 1% and not more than 70%, and in the presence of oxygen, the oxygen conversion in the process lying in the range 90 to 99%.

It is preferred to carry out the process of this invention using a catalyst in which the only catalytic oxide is bismuth oxide.

However, if desired, the catalyst may contain other metal oxides in addition to bismuth oxide, either as a support or as a co-catalyst, for example oxides of metals selected from sodium, Groups IIA, IIIA, IVA, VA, IB, IIB, IIIB, IVB, VB, VIIB, and VIII of the Periodic Table, for example alumina, magnesia. Nonacidic materials, for example silicon carbide are also useful as a support for the bismuth oxide. Some reduced bismuth oxide must be present in the catalyst. The amount of reduced bismuth oxide is likely to vary from point to point in the bed. For example, at the upstream end of the catalyst bed there may be no reduced bismuth oxide while at the opposite end the bismuth oxide may be in a very reduced state. Taken over the whole bed, the average degree of reduction lies in the range 1% to 70%. Preferably, the average degree of reduction lies in the range 2% to 50%.

Preferably, the compound $R_1 R_2 C = CR_3 CHR_4R_5$ is an olefin, for example, propylene, butene-1, butene-2, isobutene, 1-pentene, 2-pentene a methylpentene.

We have found that the gas phase oxygen profile throughout the catalyst bed has a pronounced effect upon the efficiency of the process of this invention.

The actual gas phase oxygen profile through the catalyst bed depends on the combination and interaction of a number of factors, for example the composition of the feed, the reaction temperature and pressure, and the contact time of the reactant(s) with the catalyst bed. In addition, it is preferred to keep the oxygen concentration at any point in the bed relatively low, preferably at less than 10 vol%, more preferably at less than 5 vol%. To this end, if desired the oxygen can be fed at several points along the length of the bed. A measure of the degree of oxygen conversion provides a useful guide to the oxygen profile. We have found that very suitable conditions for oxidative dimerisation occur if the degree of oxygen conversion, measured at the down-stream end of the catalyst bed, lies in the range 90 to 99%.

The preferred reaction temperature in the process of this invention is in the range 400° to 600° C., more preferably, especially when the compound being dimerised is an olefin, in the range 500° to 575° C.

In prior art processes, it is usual to employ an inert diluent with the feed. Although the use of such a diluent, for example isobutane, is not ruled out in the process of the present invention, it is preferred to operate in the absence of a diluent. This has a number of advantages, viz. a higher partial pressure of reactant leads to a larger rate of product make; a higher reaction partial pressure needs a higher oxygen partial pressure; separation of the inert gas, which may be a costly operation, is avoided.

The process may be carried out at a pressure ranging from sub-atomspheric to 50 atmospheres but it is preferred to operate at pressures no greater than 20 atmospheres so as to avoid having to use specialised pressure equipment. When operating at atmospheric pressure, a partial pressure of the compound $R_1R_2C = CR_3CHR_4R_5$ of from 0.2 to 0.99 atmosphere, more preferably greater than 0.55 atmospheres, is preferred. The partial pressure of oxygen is suitably in the range 0.01 to 0.30 atmospheres, more suitably in the range 0.05 to 0.20 atmospheres. The mole ratio of compound $R_1 R_2 C = CR_3 CHR_4 R_5$ to oxygen is preferably in the range 0.67 to 100:1, more preferably in the range 4 to 40:1.

The contact time in the process of this invention is preferably within the range 0.05 to 4 seconds, more preferably in the range 0.05 to 1 second. We prefer to use relatively short contact times since this gives less chance for a thermal reaction, generating unwanted carbon dioxide, to occur. Such a reaction occurs with long contact times and also in the absence of catalyst. Contact time also enables some control to be exerted over the product distribution. For example when reacting an olefin, the short contact time can be used to ensure that acyclic dimer rather than aromatic hydrocarbon is formed preferentially.

We have found that the process of this invention is especially useful in the oxidative dimerisation of isobutene to an acyclic dimer product. Using catalyst comprising bismuth oxide which has been reduced by an average of 2 to 70% and by keeping the oxygen conversion strictly within the limits of 90 to 99%, the conversion of isobutene is very selective to acyclic dimer product. If the average degree of reduction of the catalyst is less than 1%, then the selectivity to acyclic dimers falls severely because of the production of large amounts of carbon dioxide. If the average reduction is greater than 70%, the physical structure of the reduced catalyst begins to collapse causing a marked loss in catalyst activity.

So far as the oxygen profile is concerned, we have found that if oxygen conversion is allowed to go to 100%, then total reduction of the downstream part of the catalyst bed occurs very readily. Molten bismuth may be formed and the latter may deposit on the catalyst, thus reducing its selectivity and also causing undesired pressure drops in the reactor. Operation in the range 90 to 99% conversion enables stable conditions to be set up and readily maintained.

In the oxidative dimersation of isobutene we prefer to operate the process of the invention at a temperature in the range of 500° to 575° C., despite the fact that there are suggestions in the prior art that the dimerisation of isobutene is more readily accomplished in prior art processes at a temperature around 475° C. We have found that selectivity to the acyclic dimer is greater at the higher temperatures because the competing reaction which tends to form carbon dioxide and an aldehyde is suppressed. Furthermore, if the conversion of the olefin reactant is controlled to less than about 20% by careful adjustment of the contact time, the selectivity to the acyclic dimer (in preference to the corresponding aromatic product) is even more enhanced at the preferred higher range of temperatures.

The process of this invention is illustrated by way of Example in Examples 1 & 2 and certain features are illustrated in the Exploratory Examples.

PREPARATION OF CATALYST 93g of bismuth nitrate pentahydrate were dissolved in 100 ml of concentrated nitric acid and the solution was diluted with 200 ml of distilled water. Concentrated ammonia was added to the solution with constant stirring until no more hydrated bismuth oxide was precipitated. The precipitate was filtered out and the filter cake was carefully dried. The drying temperature of 100° C. was approached from ambient temperature by a series of 20° increments at half-hour intervals and it was maintained at 100° C. for at least 5 hours. The dried catalyst was broken and sieved into 16 to 20 mesh (1.0 to 0.71 mm) particles which were then calcined at 550° C. for at least 10 hours. This temperature was approached from ambient temperature by an increment of 50° C. in the first hour and by a series of 100° C. increments every hour thereafter. The resulting catalyst (catalyst A) was shown to be α-bismuth oxide.

EXPLORATORY EXAMPLE 1

A tubular stainless steel reactor was loaded with 1cc (2.91g) of granules of catalyst A. A stream consisting of 10% by volume isobutene and 90% by volume nitrogen (i.e. containing no oxygen) was passed over the catalyst at 550° C. over a range of contact times.

The results obtained after 5, 25 and 45 minutes running at each contact time are shown in Table 1.

TABLE 1

| Contact Time (secs) | Time of Reaction (mins) | Isobutene Conversion (%) | Selectivity to Acyclic Dimer* (%) | Selectivity to Aromatic Dimer** (%) | Selectivity to Methacrolein (%) |
| --- | --- | --- | --- | --- | --- |
| 0.05 | 5 | 3.3 | 90.4 | 1.5 | 1.5 |
| 0.05 | 25 | 2.9 | 93.2 | 0.9 | 1.7 |
| 0.05 | 45 | 2.7 | 93.2 | 1.2 | 1.5 |
| 0.10 | 5 | 5.4 | 80.5 | 3.2 | 1.9 |
| 0.10 | 25 | 5.2 | 88.0 | 1.8 | 1.5 |
| 0.10 | 45 | 4.7 | 89.0 | 1.7 | 1.0 |
| 0.30 | 5 | 13.2 | 70.8 | 8.1 | 0.9 |
| 0.30 | 25 | 10.6 | 76.5 | 5.6 | 0.7 |
| 0.30 | 45 | 9.7 | 77.2 | 5.1 | 0.7 |

*In these examples "Acyclic dimer" means a mixture of 2,5 dimethyl hexa-1,5-diene and 2,5 dimethyl-hexa-2,4-diene (in approximate ratio of 100:1).
**In these examples the "Aromatic dimer" is mainly para-xylene.

Although this Exploratory Example is not strictly an example of the process of the invention (since oxygen was absent), it provides an indication of the usefulness of partial reduction of the bismuth oxide catalyst. In general, the results in Table 1, as seen for example by comparing the results at different contact times, show that selectivity to acyclic dimer decreases with increasing isobutene conversion. The results also show that selectivity to acyclic dimer increases with increasing reaction time, and that this increase is not solely a consequence of the fall in conversion with time of reaction but results also from the increase in degree of reduction of the bismuth oxide with time of reaction. For example, after 5 minutes at a contact time of 0.05 seconds i.e. when insubstantial reduction of the bismuth oxide will have occurred, isobutene conversion is 3.3% giving a selectivity to acyclic dimer of 90.4%. However, a similar selectivity is still obtained after 45 minutes at a contact time of 0.10 seconds (when appreciable reduction of the catalyst will have occurred) and with a markedly increased conversion of isobutene (4.7%).

The results obtained at a contact time of 0.10 sec. also indicate that in the initial period up to 25 minutes, when conversion is substantially constant, there is a rapid increase in selectivity which seems to be levelling off after about 25 minutes.

EXPLORATORY EXAMPLE 2

A fresh 1cc (2.91g) sample of catalyst A was placed in the same stainless steel reactor tube as used in Exploratory Example 1. The composition of the feed was varied so that various isobutene:oxygen ratios were used for 5 minutes each. The temperature was maintained at 550° C. and the contact time at 0.17s. The results are shown in Table 2.

TABLE 2

| Isobutene Oxygen ratio | Isobutene Conversion % | Selectivity to Acyclic Dimer % | Selectivity to methacrolein % | Oxygen Conversion % |
| --- | --- | --- | --- | --- |
| 1.6:1 | 8 | 59 | 9 | 20 |
| 2.7:1 | 8 | 64 | 5 | 30 |
| 4.4:1 | 8 | 70 | 3 | 40 |

These results show that under the conditions, higher isobutene:oxygen ratios in the feed lead to a high oxygen conversion and hence a greater selectivity to the desired acyclic dimer.

EXPLORATORY EXAMPLE 3

In this example, the same catalyst loading as in Exploratory Example 2 was used. The feed used was of constant composition viz. 9% by volume isobutene, 2% by volume oxygen. The contact time was adjusted as necessary to maintain a constant conversion of 3%. The results are shown in Table 3.

TABLE 3

| Temperature °C | Selectivity to Acyclic Dimer % | Selectivity to Aromatic Dimer % | Selectivity to Methacrolein % | Oxygen Conversion % |
|---|---|---|---|---|
| 475 | 41 | 2 | 14 | 35 |
| 500 | 56 | 2 | 9 | 27 |
| 550 | 69 | 2 | 6 | 20 |
| 575 | 67 | 2 | 6 | 20 |

These results show that the greater selectivities to acyclic dimer are obtained by operating at temperatures in the area of 550° to 575° C. rather than at lower temperatures even though the oxygen conversion is lower at this higher temperature range. Thus, high selectivity to the acyclic dimer is achieved by the combination of high oxygen conversion and relatively high temperature range.

EXAMPLE 1

The tubular stainless steel reactor was loaded with a fresh charge of catalyst A, identical to that used in the Exploratory Examples 2 and 3. A mixture of isobutene and oxygen was passed over the catalyst and the various reaction parameters (other than temperature, maintained at 550° C.) were adjusted in an attempt to obtain steady operating conditions at an oxygen conversion of 94%. The results are shown in Table 4 in which it will be seen that the first three results were obtained at oxygen conversions below 90%.

TABLE 4

| Reaction Time (min) | Contact Time (secs) | Isobutene (%) | Oxygen (%) | Isobutene Conversion (%) | Oxygen Conversion (%) | Selectivity to Acyclic Dimer(%) | Selectivity to Aromatic Dimer(%) | Selectivity to methacrolein (%) |
|---|---|---|---|---|---|---|---|---|
| 5 | 0.08 | 88 | 12 | 4.5 | 42 | 57 | 2 | 25 |
| 5 | 0.08 | 95 | 5 | 2.8 | 55 | 77 | 2 | 10 |
| 5 | 0.19 | 95 | 5 | 4.8 | 68 | 84 | 2 | 5 |
| 5 | 0.19 | 96.4 | 3.6 | 4.8 | 94 | 90 | 2 | 1.4 |
| 14 | 0.19 | 96.4 | 3.6 | 4.3 | 94 | 89 | 2 | 1.4 |
| 40 | 0.19 | 96.4 | 3.6 | 4.1 | 94 | 89 | 2 | 1.4 |
| 80 | 0.19 | 96.4 | 3.6 | 4.1 | 94 | 89 | 2 | 1.4 |
| 120 | 0.19 | 96.4 | 3.6 | 4.1 | 94 | 89 | 2 | 1.4 |

In Table 4, the three results obtained at oxygen conversions below 90% indicate that in such conditions, selectivity to acyclic dimer is relatively low while selectivity to methacrolein is relatively high. However, at 94% oxygen conversion selectivity to methacrolein has fallen away almost completely while selectivity to acyclic dimer is at a favourable high level.

The catalyst, after use for 2 hours at 94% oxygen conversion, was 20% reduced although it is likely that this level of reduction was reached early in the 2-hour run and thereafter remained substantially constant. The micromeritics of the sample after use were almost exactly the same as those before use, thus indicating that the reduction had in no way affected the physical form of the catalyst. During the 2 hour period of the run at 94% oxygen conversion, the experiment was carried out under substantially constant conditions. In prior art processes, selectivity tends to fall away in the presence of oxygen. The present Example shows that there is no falling away in selectivity in the process of this invention.

EXAMPLE 2

A bismuth oxide-tin (IV)oxide catalyst was prepared by forming a paste of 69.9g bismuth oxide and 45.00g tin oxide with 60mls distilled water. The paste was dried for 12 hours at 120° C. and then calcined at 550° C. for 14 hours. The catalyst was then sieved and particles in the size range 710 to 1000µ were used in the following run.

A tubular reactor was loaded with 0.5cc (0.51g) of the thus prepared catalyst and a feed of 8.2% by volume isobutene, 1.5% oxygen and the balance nitrogen was passed over the catalyst at a contact time of 0.025sec and a reaction temperature of 548° C. After a 5 minute run, the isobutene conversion was 10.7%, the oxygen conversion was 99% with slight reduction of the catalyst. Selectivity was 77% to 2,5 dimethyl hexa-1,5-diene, 22% to carbon dioxide and 1% to carbon monoxide.

We claim:

1. A process for the oxidative dimerisation of a compound of general formula $R_1 R_2 C = CR_3 - CH.R_4 R_5$ where $R_1$, $R_2$, $R_3$, $R_4$ and $R_5$ are selected individually from hydrogen, alkyl, aryl, cyano, cyclohexyl, halide groups and substituted derivatives of these groups which comprises heating the compound $R_1 R_2 C = CR_3 - CH - R_4 R_5$ in the presence of a catalyst comprising bismuth oxide in partially reduced form, the average degree of reduction of bismuth oxide throughout the catalyst bed being at least 1% and not more than 70%, and in the presence of oxygen, the oxygen conversion in the process lying in the range 90 to 99%.

2. A process as claimed in claim 1 in which the catalyst comprises bismuth oxide with at least one other metal oxide selected from the oxides of sodium and of metals of Groups IIA, IIIA, IVA, VA, IB, IIB, IIIB, IVB, VB, VIIB and VIII of the Periodic Table.

3. A process as claimed in claim 1 or 2 in which the average degree of reduction of bismuth oxide throughout the catalyst bed is in the range of 2 to 50%.

4. A process as claimed in claim 1 in which the compound $R_1 R_2 C = CR_3 CHR_4 R_5$ is an olefin selected from propylene, butene-1, butene-2, isobutene, 1-pentene, 2-pentene, a methylpentene.

5. A process as claimed in claim 1 in which the oxygen concentration at any point in the catalyst bed is less than 10 vol %.

6. A process as claimed in claim 1 in which the process is carried out at atmospheric pressure and in which the partial pressure of the compound $R_1 R_2 C = CR_3 CHR_4 R_5$ is in the range 0.2 to 0.99 atmospheres.

7. A process as claimed in claim 1 in which the process is carried out at atmospheric pressure and in which the partial pressure of oxygen is in the range 0.01 to 0.30 atmospheres.

8. A process as claimed in claim 1 in which the mol ratio of compound $R_1 R_2 C = CR_3 CHR_4 R_5$ to oxygen is in the range 0.67 to 100:1.

9. A process as claimed in claim 1 in which the process is carried out at a contact time in the range 0.05 to 4 seconds.

10. A process as claimed in claim 1 in which the process is carried out at an olefin conversion of less than about 20%.

11. A process as claimed in claim 1 which comprises heating isobutene at a temperature in the range of 500° to 575° C. in the presence of a catalyst comprising bismuth oxide in partially reduced form, the average degree of reduction of bismuth oxide throughout the catalyst bed being in the range 2 to 50%, and in the presence of oxygen, the oxygen conversion in the process lying in the range 90 to 99% and the oxygen concentration at any point in the catalyst bed being less than 10 vol %.

* * * * *